(12) United States Patent
Sharp

(10) Patent No.: US 6,425,297 B1
(45) Date of Patent: Jul. 30, 2002

(54) NETWORKED AIR MEASUREMENT SYSTEM

(75) Inventor: Gordon P. Sharp, Newton, MA (US)

(73) Assignee: Aircuity, Inc., Newton, MA (US)

(*) Notice: Subject to any disclaimer, the term of this patent is extended or adjusted under 35 U.S.C. 154(b) by 0 days.

(21) Appl. No.: 09/677,917

(22) Filed: Oct. 3, 2000

Related U.S. Application Data

(62) Division of application No. 08/843,413, filed on Apr. 15, 1997, now Pat. No. 6,125,710.

(51) Int. Cl.$^7$ ................................................. G01N 1/00
(52) U.S. Cl. .................................................. 73/863.33
(58) Field of Search ......................... 73/863.01, 863.31, 73/863.33, 863.83, 864.34, 864.81; 454/56–62

(56) References Cited

U.S. PATENT DOCUMENTS

| | | | |
|---|---|---|---|
| 3,357,257 A | 12/1967 | Herndon et al. | 73/863.33 |
| 4,051,731 A | 10/1977 | Bohl et al. | 73/422 B |
| 4,090,392 A | * 5/1978 | Smith et al. | |
| 4,165,643 A | 8/1979 | Moll et al. | 73/863.33 |
| 4,414,858 A | 11/1983 | Peterson et al. | 73/863.33 |
| 4,499,377 A | 2/1985 | Presser | 250/343 |

(List continued on next page.)

FOREIGN PATENT DOCUMENTS

| | | | | |
|---|---|---|---|---|
| DE | 35 03 304 A | 8/1986 | | G01N/1/28 |
| DE | 41 25 739 A | 2/1993 | | G01N/1/02 |
| EP | 0 476 674 A | 3/1992 | | G01N/1/26 |
| GB | 1 252 812 A | 11/1971 | | G01N/1/26 |
| GB | 2 260 812 A | 4/1993 | | G01N/1/26 |
| JP | 61 065135 A | 4/1986 | | G01N/1/26 |

OTHER PUBLICATIONS

Sieber; "An Air Sampling System for Monitoring Carbon Dioxide Levels in Buildings" Ashrae Transactions:Symposia.*

Sieber et al., "An Air Sampling System for Monitoring Carbon Dioxide Levels in Buildings", ASHRAE Transactions: Symposia, pp. 1527–1535.

Bhaskar, R., et al., "Development of a system for analyses of airflow patterns in full–scale laboratory investigations of dust control systems," Mining Engineering, Oct. 1991, pp. 1249–1254.

"Carbon Monoxide Detection and Control Systems", Energy Controls, Inc., Jan. 15, 1986.

(List continued on next page.)

*Primary Examiner*—Robert Raevis
(74) *Attorney, Agent, or Firm*—Wolf, Greenfield & Sacks, P.C.

(57) ABSTRACT

A networked air measurement system includes a sensor capable to measuring a characteristic of an air sample, the sensor having an air inlet port; a backbone tube in communication with the air inlet port of the sensor; a plurality of air intake valves in communication with the backbone tube, air admitted through one of the plurality of air intake valves communicated into the backbone tube; an air flow induction device in communication with air in the system, air moved by the air flow induction device from the plurality of air intake valves through the backbone tube, to the sensor; and a controller connected to the sensor and to each air intake valve, the controller executing a control sequence which opens and closes air intake valves to admit air and form air samples communicated to the sensor. The system controller may use time intervals or measurements of air samples to determine proper times at which to open individual ones of the air intake valves. Furthermore, the system may include air routers and branches through which air admitted through an air intake valve may be routed to a predetermined destination. The air intake valves may be of an averaging type. The system supports a method of performing a fume hood containment test using fixed assets.

22 Claims, 10 Drawing Sheets

U.S. PATENT DOCUMENTS

| | | | |
|---|---|---|---|
| 4,601,211 A | 7/1986 | Whistler | 73/863.33 |
| 5,103,212 A | 4/1992 | Notarianni et al. | 340/628 |
| 5,246,668 A | 9/1993 | MacCallum et al. | 422/93 |
| 5,292,280 A | 3/1994 | Janu et al. | 454/229 |
| 5,293,771 A | 3/1994 | Ridenour | 73/40 |
| 5,297,421 A | 3/1994 | Hosonuma et al. | 73/40 |
| 5,357,781 A | 10/1994 | Tikjian | 73/19.1 |
| 5,390,530 A | 2/1995 | Hosonuma et al. | 73/40 |
| 5,439,414 A | 8/1995 | Jacob | |
| 5,552,763 A | 9/1996 | Kirby | 340/506 |
| 5,563,335 A * | 10/1996 | Howard | |
| 5,589,824 A | 12/1996 | Lynch | 340/628 |
| 5,764,579 A * | 6/1998 | McMasters | 454/59 |

OTHER PUBLICATIONS

Ecolyzer Product Data Sheets, National Draeger, Inc., 1984–1987.

"Model CSS Flammable Gas Detection System", Control Instruments Corp., Sep. 1980.

Moore, G. S., et al., "A sequential sampling system for multiple exposure chambers," Journal of the Air Pollution Control Association, Nov. 1979, vol. 29, No. 11, pp. 1165–1166.

National Drager, Inc. Catalog and Application Notes, National Draeger, Inc., Feb. 26, 1988.

Norman, Timothy J. et al., "Development of an Automotive–based Emission Control System for an Engine–driven Chiller", paper presented at the ASME Internal Combustion Engine Division Spring Technical Conference, Apr. 23–26, 1995.

"Sentury 5000 Gas Detection System", Sierra Monitor Corp., Apr. 1984.

"Toxic Gas Portable Analyzers, Dosimeters and Monitoring Systems", Interscan Corp.

"Toxic Systems", Sensidyne Inc., 1984.

"Underground Parking Ventilation Control System", Toxalert, Inc.

* cited by examiner

NETWORKED AIR MEASUREMENT SYSTEM

CROSS REFERENCE TO RELATED APPLICATIONS

This application is a divisional of application Ser. No. 08/843,413, filed Apr. 15, 1997, entitled NETWORKED AIR MEASUREMENT SYSTEM, and now U.S. Pat. No. 6,125,710.

BACKGROUND OF THE INVENTION

1. Field of the Invention

The invention relates to the field of environmental air management and control systems. More particularly, the invention relates to systems which sample indoor environmental air to make periodic or continuous quality measurements, including for example chemical composition, temperature, and pressure.

2. Related Art

Over the decades of the 70's, the 80's and the 90's, people have become much more energy-conscious than ever before. Among other things, this has driven the construction industry towards building structures which are far "tighter" than their predecessors, with respect to air leakage. Building designs are carefully made to provide occupants with precisely metered exchange between the indoor and outdoor air. The exchange between indoor and outdoor air is selected to provide a healthy quality of indoor air, with a minimum of energy usage for heating or cooling the outdoor air introduced. However, inevitably the tradeoff sometimes results in unacceptable indoor air quality. Moreover, the use of new building materials having many superior and desirable properties in both renovations of old buildings and new construction sometimes aggravates the air quality problems because they outgas undesirable substances. Since indoor air quality problems have a direct effect on the health of occupants of a building, there is now great interest in determining the air quality in various structures.

In laboratory settings, including chemical laboratories, biotechnological laboratories and semiconductor fabrication laboratories for example, many harmful chemicals are used. Fume hoods are used to confine and remove any harmful chemicals which may be introduced into the room by an experiment or process. Fume hoods are specially designed, confined structures in which an air flow is set up to exhaust away from a human operator any harmful substances introduced into the air. Proper operation of a fume hood requires that the air flow setting be appropriate for various parameters, including the size of the opening through which the operator may need to manipulate equipment in the hood, the supply of makeup air into the laboratory room in which the fume hood is located, and the type of materials and experiments being performed in the hood, for example. Fume hoods therefore typically include a controller which responds to various settings and determines a proper air flow through the hood. The controller then sets appropriate valve positions, fan settings, etc. to achieve the desired air flow setting. However, if a human operator improperly sets a parameter in the controller, or if the controller or a controlled element fails, then the proper air flow may not be set, resulting in a "spill" of some substance from inside the fume hood into the indoor air of the human operator. Such a spill may have a minor effect on indoor air quality or may be extremely hazardous, depending on the nature of the substance spilled and the size of the spill. Detecting spills quickly is important both for evacuating areas in a timely manner if required, and for correcting the problem which caused the spill in the first place.

Both of the areas of concern discussed above have resulted in a great deal of work in the area of measuring indoor air quality. A wide variety of sensors are available, for measuring temperature, humidity, CO2, CO, volatile organic compounds (VOCs), smoke, various other chemical contaminants, particulate levels, dust, animal odors sch as caused by rat urine proteins (RUPs), etc.

In one prior approach, shown in FIG. 10, to the problem of measuring indoor air quality, remote sensors for each of the substances or parameters of indoor air quality desired to be measured are placed at each site of interest within a structure. In one variation, the sensors may simply record their measurements locally, for later collection while in another variation they may be connected through electronic wiring to a central data collection system.

One major problem with local data collection is that it is useless for real time control, since the data is not available, except when collected. With a remote sensor system having central data collection, the data is available whenever the central system polls each particular sensor. However, another major problem with remote sensor systems is that they require the use of a multiplicity of expensive sensors at the individual sites to be measured. The expense is very high and the system is fairly inflexible. If a new parameter needs to be measured throughout a structure, a multiplicity of new sensors need to be installed at all the relevant sites.

Another approach to the problem, shown in FIG. 11, is a multiple point, sequenced system including a central computerized sensing system having a plurality of input ports connected via hollow tubes to each room of interest. A vacuum system is used to draw air samples through the tubes from each room down to the central sensing system, where a single sensor suite sequentially performs measurements on each of the air samples obtained. This system is far less expensive than those described above because it only uses one set of sensors. It is also far more flexible, in one sense, because there is only one sensor suite to be changed, if the measurements desired should change.

However, this approach is still relatively inflexible and expensive to install because of the large bundle of individual sensing tubes which must be run from the central sensing location to each site from which a sample is desired. There is also a cost associated with unused capacity held in reserve to receive additional sensing tubes at the central computerized sensing system, should potential changes to the structure requiring additional sampling sites be implemented. Such changes are common in both office and laboratory settings, where space is frequently divided and consolidated as the goals and tasks of organizations change.

Yet another conventional approach to this problem is a centralized sensing system having a single sample tube. The sample tube is snaked through the building to each space where it is desired to take an air sample. A hole is made in the sample tube at each point where an air sample is desired to be drawn from. However, such a system is extremely limited since the system makes a single, "mixed" measurement of the air drawn in through the holes in the sample tube. In other words, this system uses the sample tube as a mixing chamber in which the air drawn in through the holes is blended or homogenized into a single sample. This system lacks the capability to make individual measurements of the air drawn in through each separate hole. Rather, averaged measurements of desired parameters are made.

SUMMARY OF THE INVENTION

Therefore, it is desired to provide an air sampling system which solves the above noted problems. It is desired to provide an air sampling system which provides data to a central system, whereby building elements affecting air flow near a sampling site may be controlled in response to changes in local air quality. It is desired to provide an air sampling system in which installation costs are relatively low and flexibility is relatively high.

Embodiments of the present invention can be installed in parallel with the electrical and pneumatic networks conventionally used in modern construction. Hence, installation cost is kept low. In many installations, Phoenix Controls Corporation electronically controlled valves or other electronically controlled valves or airflow controls will be used throughout. In such cases, an embodiment of the invention may use the valve sites as junction sites. Some inexpensive system components may even be preinstalled at other junction sites in anticipation of future expansion. By so doing, great flexibility is achieved at minimal cost.

Various aspects of the present invention described below address these concerns and such others as will become evident to those skilled in this art.

According to one aspect of the invention, there is provided a networked air measurement system including a sensor capable of measuring a characteristic of an air sample. Suitable sensors typically have an air inlet port through which an air sample, comprising a small quantity of air to be measured may enter the sensor and an exhaust port through which the air sample may exit the sensor. The characteristics which such sensors measure may include, but are not limited to, temperature, humidity, pressure, particulate levels and contaminant levels (e.g., CO, $CO_2$, VOCs, RUPs, etc.) A backbone tube is in communication with the air inlet port of the sensor. The backbone tube may be a length of pneumatic tubing, for example of a plastic or metal. A plurality of air intake valves in communication with the backbone tube admit air into the backbone tube. The air intake valves may be any suitable remotely controlled intake valves. They may be solenoid or poppet valves, pneumatic valves, gate valves, butterfly valves or other substantially two-position valves, for example. An air flow induction device in communication with air in the system moves air from the plurality of air intake valves through the backbone tube, to the sensor. The air flow induction device may be an exhaust blower, air compressor or vacuum pump connected to produce a low pressure at the exhaust port of the sensor, for example. Other air induction devices can be used, such as a ducted blower connected between the backbone tube and the inlet port of the sensor. A controller connected to the sensor and to each air intake valve executes a control sequence which opens and closes air intake valves to admit air and form air samples communicated to the sensor. A suitable controller may be a personal computer or microprocessor unit executing special-purpose software, for example. This basic system is subject to numerous useful variations.

Enhancements to the tubing portion of the system are possible. For example, the system may further include a plurality of branch tubes connected between the backbone tube and each one of the plurality of air intake valves, bringing each one of the plurality of air intake valves into communication with the backbone tube. Further enhancements to the controller are possible. For example, the controller may execute a control sequence in which each one of the plurality of air intake valves is opened and closed at individually defined times which result in a separate air sample from each one of the plurality of air intake valves being communicated through the backbone tube to the sensor. In addition, the controller may execute a control sequence in which predefined groups of air intake valves are opened and closed substantially in unison, a measurement is made by the sensor, and each one of the plurality of air intake valves is opened and closed at individually defined times only when the measurement meets predefined criteria. In another variation of the controller, a measurement may be made by the sensor and the controller may monitor the measurement to determine when a stable air sample is achieved. In yet another variation on the controller, the controller may include a timer which is monitored by the controller to determine that a stable air sample is achieved after a predetermined interval, the predetermined interval individually defined for each one of the plurality of air intake valves. Finally, the controller may monitor a measurement made by the sensor after the predetermined interval, the controller determining from the measurement that a stable air sample is achieved.

In other variations the air samples taken may be directed through the system. For example, there may be an air sample router connected between the backbone tube and a group of the plurality of branch tubes. The air sample router and the air flow induction device may then be controlled by the controller to route air admitted through one of the plurality of air intake valves to a destination. In a further variation, there may be a second sensor in communication with the backbone tube through a branch tube and the air sample router, wherein the destination of the air admitted through one of the plurality of air intake valves is the second sensor.

Some variations on the air intake valves are contemplated. An air intake valve may provide an average sample from an air flow. Such a valve may include an high pressure inlet port; an averaging chamber in communication with the high-pressure inlet port, air admitted through the inlet port over a time interval being mingled in the averaging chamber; a low pressure outlet port in communication with the averaging chamber, air being exhausted from the averaging chamber through the low-pressure outlet port; and a solenoid valve in communication with the averaging chamber and the backbone tube, through which air from the averaging chamber is admitted to the backbone tube. In this type of valve, the inlet port and the outlet port may be disposed on a high-pressure side and a low-pressure side respectively of an air flow control device, such as a room exhaust valve or a room make-up air supply valve. Alternatively, the inlet port may be disposed in a room air space when a room exhaust valve is used.

According to another aspect of the invention, a method of measuring air quality at a plurality of sites, may include the steps of: drawing a plurality of air samples from the plurality of sites into a common inlet tube; moving the plurality of air samples through the common inlet tube from the plurality of sites to a common sensor at a fixed location, substantially without mixing the air samples with each other due to time sequencing of the samples; and measuring a parameter of each of the plurality of separate air samples. The step of drawing may further include drawing one air sample over a period of time, whereby the one air sample averages the parameter over the period of time during which the air sample is drawn.

Numerous other variations and combinations contemplated by the inventor as within the spirit and scope of the invention will now be apparent to those skilled in the art.

BRIEF DESCRIPTION OF THE DRAWINGS

In the drawings, in which like reference numerals denote like elements.

DETAILED DESCRIPTION

The present invention will be better understood upon reading the following description of embodiments thereof, in connection with the figures.

Figure 1:
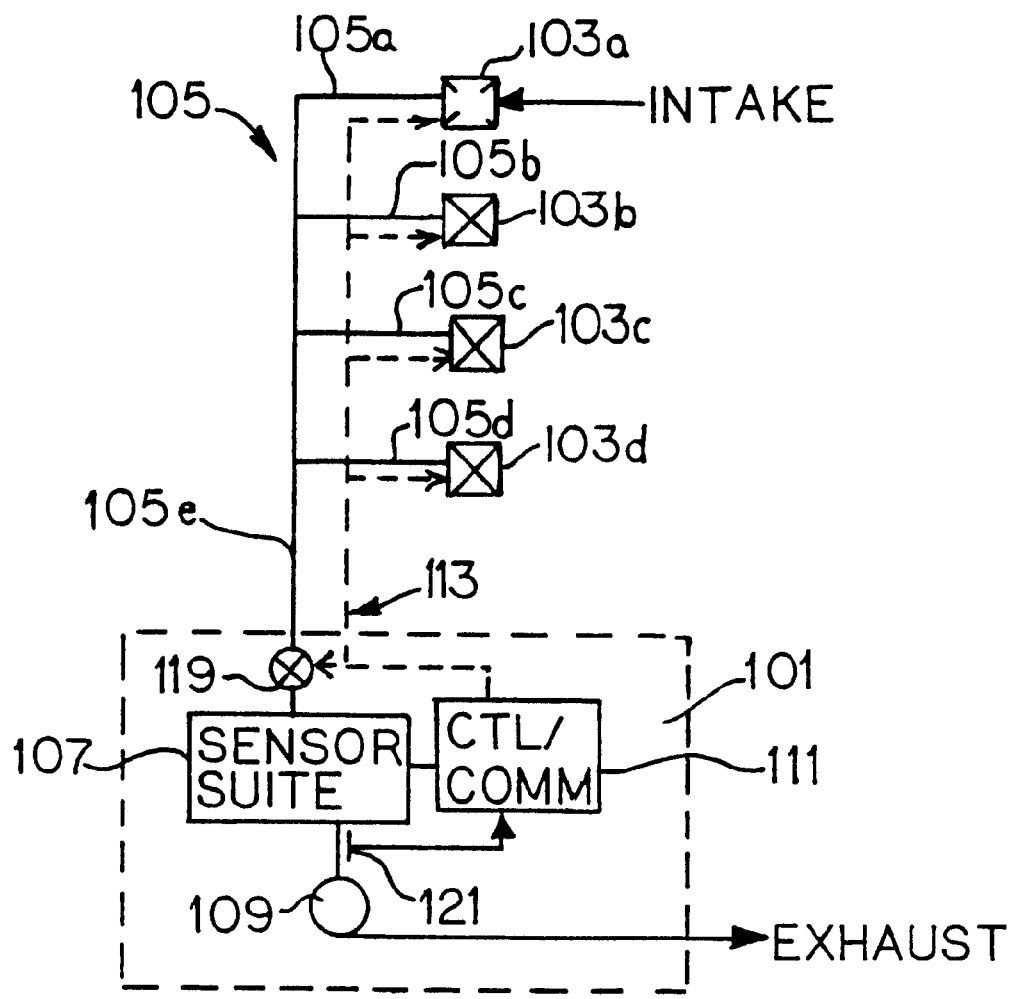
FIG. 1 is a schematic drawing of an embodiment of an air sampling system illustrating some aspects of the invention.

As shown in FIG. 1, a simple system embodying some aspects of the present invention includes a central sensing and control system 101 connected to a plurality of air intake valves 103a–103d through a network of tubing 105. The network of tubing 105 has a backbone section 105e and branches 105a–105d corresponding to and connected to respective air intake valves 103a–103d. The central sensing and control system 101 includes a sensor suite 107 connected to an end of tubing backbone section 105e, an air pump 109 connected to the sensor suite 107 to draw air through the system, and a control and communications unit 111 for controlling operation of the sensor suite 107, the air intake valves 103a–103d, and the air pump 109, as well as communicating with the sensor suite 107 and external equipment. The control and communications unit 111 can control the various elements through a fiber optic, electronic or pneumatic control network 113, including network device adapters 115 for input/output functions and control network routers 117 for controlling communication within the control network. Alternatively, the network device adapters 115 and control network routers 117 can be omitted, with the control and communications unit 111 communicating directly with the controlled elements, such as valves 103. Embodiments of the invention will generally employ a digital communications network as the control network 113. For example, the network may be that described in the inventor's U.S. Pat. No. 5,831,848, entitled DISTRIBUTED ENVIRONMENTAL PROCESS CONTROL SYSTEM, filed Nov. 17, 1995, issued Nov. 3, 1998. Other known network types, such as Ethernet, Arcnet or approaches using Echelon Lonworks can also be used.

While the air pump 109 draws air through the system, the control and communications unit 111 operates the air intake valves 103a–103d in a sequence, so that each valve (e.g. valve 103a) is open for a time while the others (e.g. valves 103b–103d) are closed, thus drawing an air sample into the system from a sample site at which the open valve (e.g. valve 103a) is located. In the configuration of FIG. 1, air samples from a plurality of valves (e.g., 103a–103d) are drawn in the control sensing and control system 101 through a single backbone section 105e. Sensor suite 107 thus has only one inlet port to which backbone section of tubing 105e is connected.

The sensor suite 107 measures various parameters of the air sample passing therethrough. Individual sensors within the sensor suite 107 may be arranged to receive air from the inlet either in series or in parallel, depending upon the flow rate requirements, pressure requirements and effects of the sensors on the sample chemistry or other properties. In a series connection, the air sample passes through each series-connected sensor in sequence, while in a parallel connection the air sample passes through each parallel-connected sensor at the same time. The control and communications unit 111 reads the measurements made by the sensor suite 107 and communicates the readings to external equipment (not shown) such as building air flow controls, fume hood controllers, etc. Either the control and communications unit 111 or the external equipment may use the data collected in a variety of ways, including, but not limited to passive data collecting, activating alarm mechanisms under specified conditions, activating safety mechanisms under specified conditions, and changing local or overall air flow parameters by issuing commands to the air flow control equipment. This embodiment of the invention may thus form part of an integrated overall approach to air quality measurement, control and management.

In a related aspect to this and other embodiments of the invention, the control and communications unit 111 includes either a computer or microprocessor executing a software or firmware program or specialized hardware for ensuring that the sample measured by the sensor suite 107 is in fact that taken in through an open air intake valve (e.g. 103a). It will be appreciated by those skilled in this art that the speed of the air flow through the system is finite. Therefore, there is a finite delay between the time a particular air intake valve (e.g. 103a) is opened and the time when the sample thus obtained reaches the sensor suite 107. Purging the system between samples in a conventional sense is unnecessary. Each sample may be thought of as a "packet", much as information networks move packets in a time-ordered sequence. It is believed in a system of this type that air samples of sufficient size do not mix appreciably with each other, except to a small degree at the interface between successive samples. Thus, the sample itself purges the system to whatever degree is necessary to obtain a stable sample.

Several techniques are available for ensuring that measurements of samples do not occur at the interface between successive samples. In one technique, the known time delays of samples traveling between different parts of the system may be relied upon. In another technique, the stream of samples may be continuously monitored for characteristics indicating that a measurement is being taken in mid-sample. Finally, these techniques may be combined to exploit the advantages of each.

According to a first technique, each air intake valve 103a–103d is opened in a sequence 103d→103c→103b→103a, drawing four corresponding samples D, C, B and A into the sensor unit 107. The time and duration of opening each valve is selected to be long enough for a stable sample larger than the intersample interface volume to be obtained through the air intake valve 103a–103d, thus ensuring a good sample reaching the sensor unit 107 regardless of whether there is a next upstream air intake valve 103a–103d to be opened in the sequence. The time for sample A to travel from air intake valve 103a to the sensor unit 107, $T_A$, is assumed to be known, for example by prior measurement. When the time $T_A$ has passed from the opening of air intake valve 103a, plus an additional time necessary to move the portion of the sample A in the sensor unit 107 beyond any interface volume between the sample A and an adjacent prior sample, then the sensor unit 107 performs the measurements for which it is equipped.

According to a second technique, each air intake valve 103a–103d is opened in a sequence 103a→103b→103c→103d, drawing four corresponding samples A, B, C and D into the sensor unit 107. Also as described above each valve is held open for a time sufficient for a stable sample to be drawn past the next downstream air intake valve to be opened in the sequence. The time is again selected to be sufficient for a stable sample, larger than the intersample interface volume, to be obtained through the air intake valve 103a–103d, thus ensuring a good sample reaching the sensor unit 107 regardless of whether there is a next downstream air intake valve 103a–103d to be opened in the sequence. As above, measurements may be timed to occur at times defined by the known travel times $T_A$–$T_D$ after each valve 103a–103d has opened and the interface volume transit time through the sensor unit 107.

Instead of timing, a third technique relies on measuring the samples A–D which are large enough to produce stable measurements over a substantial period of time ranging from a few milliseconds to a few seconds. The sensor unit 107 is continually operated and monitored to determine the dynamic characteristics of the air stream flowing past the sensors contained therein. During times when the measurements are changing, the intersample interface is passing through the sensor unit 107. During times when the measurements are substantially stable, the useful stable portion of a sample is passing through the sensor unit 107. The sensor unit 107 may be connected to a control system 111 which uses past measurement data to estimate when each future sample will be valid. The above methods can be combined in an embodiment of the invention in which a computer-based data processing system executing a software program monitors the measurements made by sensor unit 107 and makes a determination of when the measurements are valid measurements of the stable portion of a sample, for example using a heuristic method which depends both upon sample transit times determined by previous sample measurements and upon the stability of the current measurement.

Techniques dependent only on timing provide coarse information about which sample is passing through the sensor unit 107, while techniques which add measurement stability and past performance fine tune the measurement to the most stable portion of the sample. By combining the coarse and fine determination of the proper portion of the sample, for example the order of the sequence may be varied, while accurate measurements of each sample continue to be obtained because the system has a priori knowledge of which sample will pass through the sensor unit 107 at what time. Moreover, if power variations to the air pump 109 or other environmental variations cause the delay times through the system to vary by a small amount, the fine tuning aspect of the second technique can correctly identify the appropriate portion of each sample to measure. It is also possible to open a plurality of the air intake valves simultaneously, producing a mixed sample. If the sensor detects a predetermined characteristic in the mixed sample, for example an excessive level of a contaminant, then sequencing such as described above may be performed.

In one use of the above technique, an outbreak of fire or chemical spill can be quickly identified, isolated and reacted to. Each mixed sample could be evaluated by a plurality of sensors which are selected to detect combustion products or chemical contaminants known to be stored or used in the building environment. When one of these combustion products or contaminants are detected in the mixed sample, a first alarm level may be triggered. The sensor which triggered the first alarm level may then be used to measure individual samples drawn in sequence from each intake valve. The system then identifies which building space is the source of the combustion product or contaminant. A second alarm level may then be triggered for the affected space. The second alarm level may be communicated by the control unit to fire suppression systems, ventilation/purging systems, evacuation alarms and emergency services personnel, for example.

The technique just described is particularly useful for achieving reduced cycle times in systems employing sensors for multiple parameters. The mixed sample may be evaluated by a plurality of sensors operating in sequence or simultaneously on the same air sample. Only when a first level alarm is triggered, or at less frequent, predetermined intervals, would individual samples from each of the intake valves be taken. Far fewer samples are required during periods when no alarm is triggered because it is not necessary to always measure a sample from each intake valve with each sensor. Even during an alarm, the system can focus measurements on one or more affected sensors and one or more affected intake valves.

In the above-described system, the tubing used throughout should be of a material which is resilient, for easy installation, and which is resistant to the various chemicals which might be found in the installation site. For some installations, the preferred tubing is formed of high density polyethylene (HDPE) because it is both resilient and chemically resistant. In applications including particle detection, a conductive plastic or copper tube which can be grounded may be preferred. When particle detection is included, it is desirable to avoid tubing which can build up a static electric charge which may attract particles out of the samples, leading to measurement errors. Those skilled in this art would be able to select a suitable tubing material for a particular installation, depending upon such factors as the expected materials in the building environment, environmental temperatures and pressures, parameters to be measured, and cost, for example.

The maximum sample velocities achievable through the tubing 105 establish the minimum cycle time for a system based upon the run lengths involved. As an example, consider a system designed to react to changes in air quality within a time of 10 seconds. Then each sample must reach the sensor unit 107 within a time less than 10 seconds in order to be measured and reacted to. The maximum velocity of the air sample stream is a function of the allowable pressure drop of the system, the allowable change in density of the sample that results, the tube and inlet valve diameter and resistance, and the desired sample flow rate into the inlet valves 103. Atmospheric pressure of 15 PSI puts an upper limit on the allowable pressure drop. However, in practice, the allowable pressure drop is less because of the effect a pressure drop has on the sample. For example, a pressure drop may affect the relative humidity or temperature of a sample, or cause a target contaminant to precipitate out of the sample. Numerous other detrimental effects may also be seen. The inventor has found a 10 PSI pressure drop (to 5 PSI absolute) to be a tolerable maximum for many purposes. Systems which exhibit lower pressure drops, for example in a range of 3–5 PSI, have greater flexibility because there is more margin before the pressure drop adversely affects the samples. Moreover, transit times in such systems are more readily calculable since sample speed varies inversely with the pressure of the sample. In a system with greater pressure drops, as the sample travels from an open intake valve, through a length of tubing, perhaps through a router, and eventually to the sensor suite, the pressure in the sample drops significantly. That variation in sample pressure causes a corresponding variation in sample speed, making the overall speed through the system variable, depending upon where a sample starts from and what system elements (having what pressure drops) it passes through. An example of the effect of distance on pressure drop and transit time is shown in Table 1, below, for a system operating with an intake valve volumetric flow rate of about 250 SCIM (standard cubic inches per minute) and having a tube inner diameter of 0.17". Such a system has a useful recommended run length of no more than about 500 ft. By comparison, if the same system were operated at only 125 SCIM, the maximum run length exceeds 1,000 ft., as seen in Table 2.

TABLE 1

0.17" tube inner diameter (ID)
250 SCIM (Standard cubic inches per minute) (4 lpm)
Inlet valve pressure drop: 0.75 PSI

| Feet of tubing | Pressure at sensors | Transit time of packet | Velocity in tubing at sensor suite |
|---|---|---|---|
| 100 | 13.4 PSI | 6.2 sec | 1000 FPM |
| 500 | 9.7 PSI | 26 sec | 1390 FPM |

TABLE 2

125 SCIM
Inlet valve pressure drop: 0.19 PSI

| Feet of tubing | Pressure at sensors | Transit time of packet | Velocity in tubing at sensor suite |
|---|---|---|---|
| 100 | 14.6 PSI | 13 sec | 455 FPM |
| 500 | 13.7 PSI | 62 sec | 494 FPM |
| 1000 | 12.4 PSI | 119 sec | 544 FPM |

For many types of measurements, the flow rate, density and volume of the sample measured affects the measurement. For example, in systems measuring particulate content, flow velocities exceeding about 1200 FPM are desired to prevent deposition of the particulate matter on the tube walls. Therefore, flow rate through the system should generally be regulated. A venturi valve, a pressure regulating valve or a mass flow control valve could be used to regulate flow. See FIG. 1, 119. A mass flow control valve has a further advantage in that it can help control sample density, as well. Alternatively, vacuum at the sensor suite or at the pump may be actively regulated by varying pump or blower speed, air flow throttle position, damper position, etc. This could be done by using an absolute pressure sensor or vacuum pressure sensor (see FIG. 1, 121) measuring the pressure at the inlet or outlet of the sensor suite or the pump or some other point in the system to optimize controllability. A small vacuum, e.g., 10–12 PSI absolute pressure, maximized sample density and minimized sample volume. A large vacuum, e.g., approximately 5 PSI absolute pressure, minimizes transit time. The choice of pressure or flow control or a combination thereof is a design choice which depends upon the parameters to be measured and functions to be performed, and is best left to the system designers. Those skilled in the art will appreciate how to compute useful maximum velocities or determine them through modeling techniques.

As can be seen in Tables 1 and 2, the maximum usable run length depends upon the desired velocity and the maximum allowed pressure drop. Skilled designers will trade off between these parameters to optimize designs for particular purposes. Such maximum run lengths can limit the applicability of the system of FIG. 1, but the inventor has proposed a system as shown in FIG. 2 which overcomes this problem for large systems. The embodiment shown in FIG. 2 also has several additional advantages, which are now discussed.

The more extensive system of FIG. 2, illustrating additional aspects of the invention, includes the central sensing and control unit 101, as described above. In addition, the central sensing and control unit 101 is connected through tubing network 105 to a plurality of air intake valves 103, as now described.

In this embodiment, several subnetworks are defined by backbone sections **105*f*–105*k* each connected to a main backbone including segments 105*e*–105*n* of tubing network 105 through routers 201. The routers 201 are air flow switches, for example controlled electronically or pneumatically by control and communication unit 111 of the central sensing and control unit 101. The routers 201, shown in greater detail in FIGS. 4A–4C, are described below. Alternatively, there may be an external control system (not shown) which operates both the routers 201 and the air intake valves 103 of this embodiment. Finally, this system can include distributed sourcing/sensing packages 203, connected to at least some branches (e.g. 105*a*–105*c*) of tubing 105. The distributed sourcing/sensing packages 203 may include one or more sensors and an air pump connected to draw air from the branch of tubing 105**, through the sensors.

The system of FIG. 2 introduces a significant degree of flexibility and redundancy. By selectively setting the connections made by each of the routers 201 and by selectively opening one of the air intake valves 103, an air sample may be routed from any air intake valve 103 site to any sensor 101 or 203. One use for such a structure is to incorporate one or more redundant sensors for a critical parameter into distributed sensing packages 203. Thus, if a primary sensor for the critical parameter (e.g. in central sensing and control unit 101) should fail, samples may be rerouted to the redundant sensor for obtaining a valid measurement. Similarly, by making appropriate connections in the routers 201, multiple, simultaneous measurements may be taken using sensors from different units 101 and 203. By employing redundant sensors for a critical parameter, the cycle time for the critical parameter may be reduced as a result of greater sensor availability.

Another way the system of FIG. 2 may be used is to make continuous measurements, for example of modest accuracy or omitting one or more parameters of interest, at sensors 203, and more precise or more complete measurements at central sensing unit 101. The more precise or more complete measurements can be made when one of the sensors 203 detects an alarm condition, in order to verify the condition.

The more complete, possibly more expensive set of sensors provided in control sensing unit 101 need not be fully duplicated in sensors 203.

Figure 2:
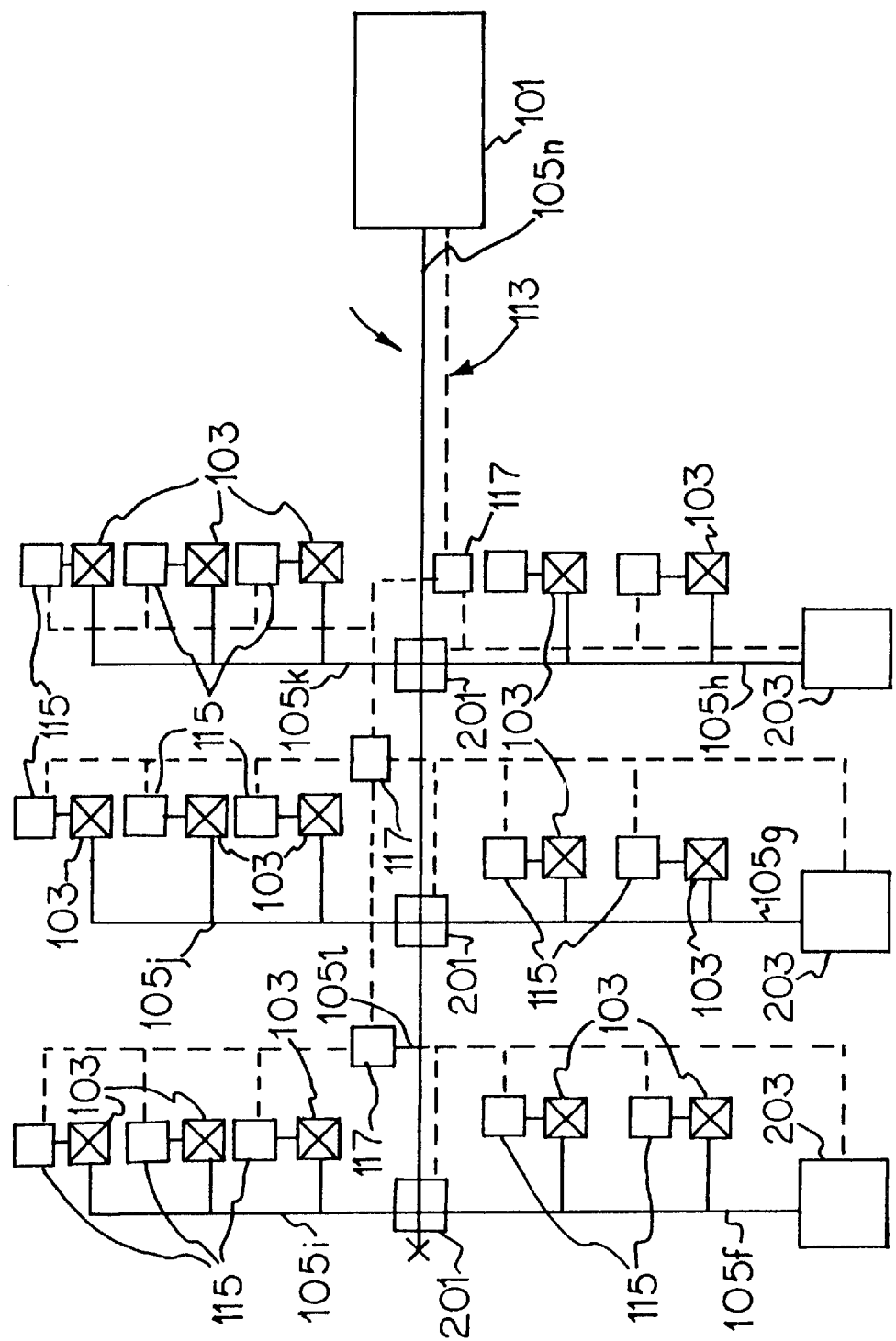
FIG. 2 is a schematic drawing of another embodiment of an air sampling system illustrating additional aspects of the invention.

The system of FIG. 2 is partially de-centralized, but has several advantages over a conventional remote sensor system. For example, the system does not require a sensor suite for every location at which measurements are desired. The system is readily expanded by simply adding routers, tubing and valves where required. The electronic network through which data is transferred and control is achieved may be installed in parallel with the network of air tubing.

The system described above with respect to FIG. 2 may, in a variation, be used to inject a tracer gas into one or more of the sites and measure the dispersion of the tracer gas to any one or more of the sites. Distributed sourcing/sensing units 203 could include tracer gas or particle sources, including an air pump connected to blow tracer gas or particles through tube network 105 under pressure from a distributed sourcing/sensing unit 203 to an open air intake valve 103, which then operates as a tracer gas or particle outlet valve. After injecting a tracer gas or stream of particles, the source may be turned off and the system operated as a sensing system to detect to which air intake valves 103 the tracer gas or particles may migrate over some period of time. Alternatively, the tubes 105a–105i may be of a twin-tube type commonly used in air management systems. Twin-tube tubing is a conventional, off-the-shelf product. The twin-tube arrangement permits two different samples to travel in different directions through the system, simultaneously. For example, a tracer gas or particles may be injected through one tube of a twin tube while a sample is taken through the other. A twin-tube network system can be configured to significantly reduce cycle times, by allowing air packets to be independently routed in different directions, to different sensor suites at the same time. Moreover, by switching the sourcing and sampling functions between adjacent tubes of a twin tube branch, the tubes can be cleared of undesired contamination between measurement cycles using a clean flushing material in a similar manner to the method for supplying a tracer gas through the system. Also, by injecting a calibrated tracer material, for example one with a known concentration of a specified contaminant, through one tube and routing it to one of the remote sensor units 203, the remote sensor units 203 can be calibrated automatically, without being removed from the system or directly accessed.

Some variations and applications of the systems described thus far are now discussed.

One type of environmental air quality monitoring important to owners of laboratories is that of monitoring fume hood containment performance. The American National Standards Institute ("ANSI"), in conjunction with industry organization, ASHRAE, has established the ANSI/ASHRAE 110–1995("ASHRAE 110") test as a standard procedure for establishing, among other factors, fume hood containment performance. The 1995 edition of the ASHRAE 110 specification is incorporated herein by reference.

The ASHRAE 110 test calls for the introduction of a tracer gas into the internal work space of a laboratory fume hood, while dispersion of the tracer gas into a region of the laboratory in front of the hood sash is monitored. In order to create more realistic airflow patterns in the vicinity of the hood, the sensor employed is mounted in a manikin positioned where a laboratory worker would typically stand in front of the hood sash. Conventionally, the ASHRAE 110 test is performed by a skilled consultant using specialized equipment costing $10,000 or more. Each test performed on each hood at a laboratory site can cost $500–$1,000, including set-up, tear-down, consultant's fees, travel costs (for the consultant), etc.

The system according to the invention can perform the same or a similar test at a significantly lower cost of about $150–$200 per hood. A twin-tube embodiment of the invention is a network capable of delivering a tracer gas from a small number of central sources to multiple fume hoods throughout a building, while simultaneously drawing and measuring air samples from the vicinity of each fume hood.

A system to perform a standard ASHRAE 110 fume hood containment test would terminate one tube at a valve inside the fume hood. That tube and valve is operated to deliver tracer gas at the flow rate specified in the AGHRAE 110 standard.

Such a system would terminate the second tube at a receptacle suitably located in the vicinity of the fume hood sash. A manikin fitted with an intake tube at a location defined by the ASHRAE 110 specification is stood at the specified position; the intake tube then being plugged into the receptacle. Thus, air samples are taken through the intake tube as specified by ASHRAE 110, and delivered to centrally located sensors, including a sensor for the tracer gas.

A system according to the invention could also be configured to run a continuous or frequent periodic fume hood containment test as follows. Tracer gas can be delivered as described above. Air samples can be drawn through intake valves suitably located in the vicinity of the fume hood sash. Although the intake valves need not be located in a manikin as specified in the ASHRAE 110 standard, suitably located intakes, for example attached to the front frame of the fume hood sash as well as to the bottom of the sash, would provide significant and useful test results. Such a continuous or frequent periodic test could be used in connection with direct control of fume hood operation or in order to ensure better compliance with safety requirements than might be obtained through annual ASHRAE 110 testing. Also, the invention is not limited to the particular tracer gas or flow rate specified in ASHRAE 110. Other gases and flow rates will be effective in such a system, as is known to those skilled in this art. By using such a substitute, significant additional cost savings may be realized, by use of a cheaper tracer gas and sensor combination which may provide substantially similar sensitivity performance as the gas and sensor specified by ASHRAE 110.

Some uses of embodiments of the invention to discharge a tracer gas into an environment have been described. However, the use of the invention to discharge materials into the environment is not limited to tracer gases, or to the applications discussed so far. For example, clean room systems can be tested by injecting a test particulate which should be cleared by the clean room filters. The sensor suite can include a particle counter measurement for this application. In another example, the system could simply inject an odorant or decontamination chemical either periodically or when measured conditions indicate a need to mask odors or decontaminate an area. Since materials can be routed from any source to any destination in the network, injection of materials and measurement of results can be performed by a single network.

Another application achievable by the invention is measurement of pressure in remote locations. Such a measurement simply requires opening one intake valve in the network while closing off with a valve any tubing leading to the vacuum pump 109 or any other opening to the atmosphere. A pressure sensor anywhere in the network will then indicate the pressure at the open intake valve. In a large network, it is advantageous to use the routing valves to close off unused portions of the network during this measurement, since reducing the volume of tubing whose pressure must be equalized speeds up the stabilization and measurement. For this reason, a network configured as shown in FIG. 2, with pressure sensors located in the remote sensor suites 203, is advantageous in pressure sensing situations.

Embodiments of the invention can also be configured to perform differential pressure measurements across valves, between rooms in a building, between a room and an adjacent corridor, etc. Differential pressure can be measured by performing a pressure measurement at a first location as described above, followed by performing a pressure measurement at a second location also as described above. Pressure sensors in the remote sensor suites 203, which are closer to some intakes, can provide a faster pressure reading for this type of measurement because more of the network can be cut off by the routers from the portion needed to take the pressure measurement, than might be the case if the measurement were made by the central sensor suite 101.

Plural pressure sensors located in the central sensor suite 101 and in the remote sensor suites 203 can be calibrated by taking a pressure measurement of a common intake or a common source of a known pressure with each sensor and comparing the results.

In some useful systems embodying the present invention, it may be desirable to measure within an air flow average values of some parameters. Averaging air intake valves are shown and described in connection with FIGS. 3A–3C. Any of the valves denoted 103a–103c in FIG. 1 and 103a–103f in FIG. 2 may by of one of the averaging types shown schematically in FIGS. 3A–3C.

Figure 3A:
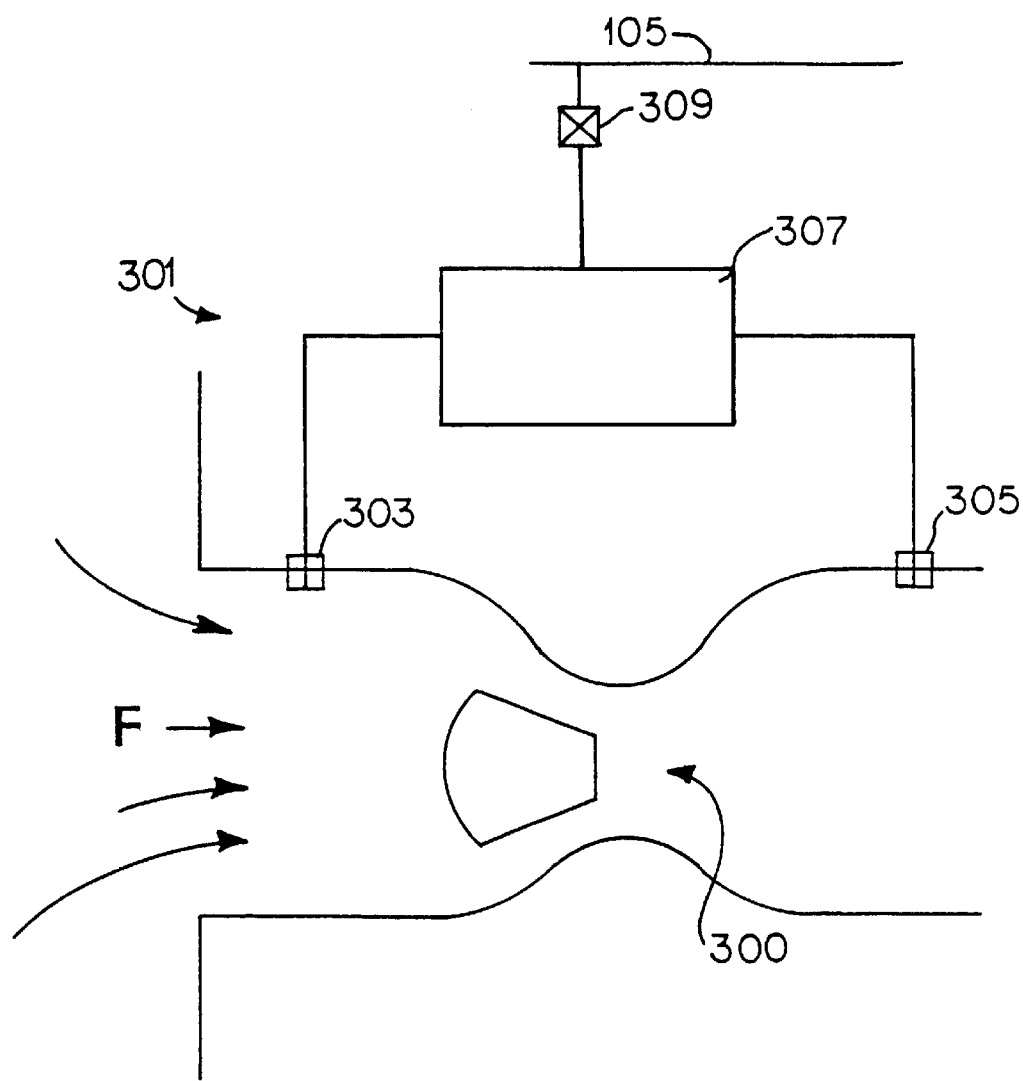
FIGS. 3A–3C are schematic drawings of averaging air intake valves useful in some embodiments of the invention.

FIG. 3A illustrates a configuration for taking an average sample in an exhaust duct flow. The averaging air intake valve 301 is connected through a pair of pressure taps 303 and 305 to straddle an exhaust valve 300 in the exhaust duct in which the sample is taken. Instead of straddling an exhaust valve 300, the averaging air intake valve 301 could be connected to straddle another device which creates a pressure drop within an air flow. For example, the averaging air intake valve 301 could straddle an airflow controller, a damper, an orifice ring, an elbow or simply a restricted length of duct. The averaging air intake valve 301 includes between pressure taps 303 and 305 a sampling chamber or bag 307. Assuming the air flow through the exhaust valve 300 to be in a direction F, there is a high relative air pressure at pressure tap 303 and a low relative air pressure at pressure tap 305. Therefore, a small portion of the air flow through exhaust valve 300 is bled off by pressure tap 303, and diverted into the sampling chamber 307. Some of the air already in the sampling chamber 307 is returned to the exhaust flow, just downstream of the exhaust valve 300. The sample in the sampling chamber 307 contains a mixture of air from the flow, retained in the sampling chamber 307 for a period of time. The sample thus forms an average of the contents of the flow over the period of time. The sampling chamber is connected to the tubing 105 through a solenoid valve 309, or other suitable device for controlling when a sample is drawn into the system. An averaging air intake valve 301, thus configured may replace any of the air intake valves 103a–103f previously discussed.

Figure 3B:
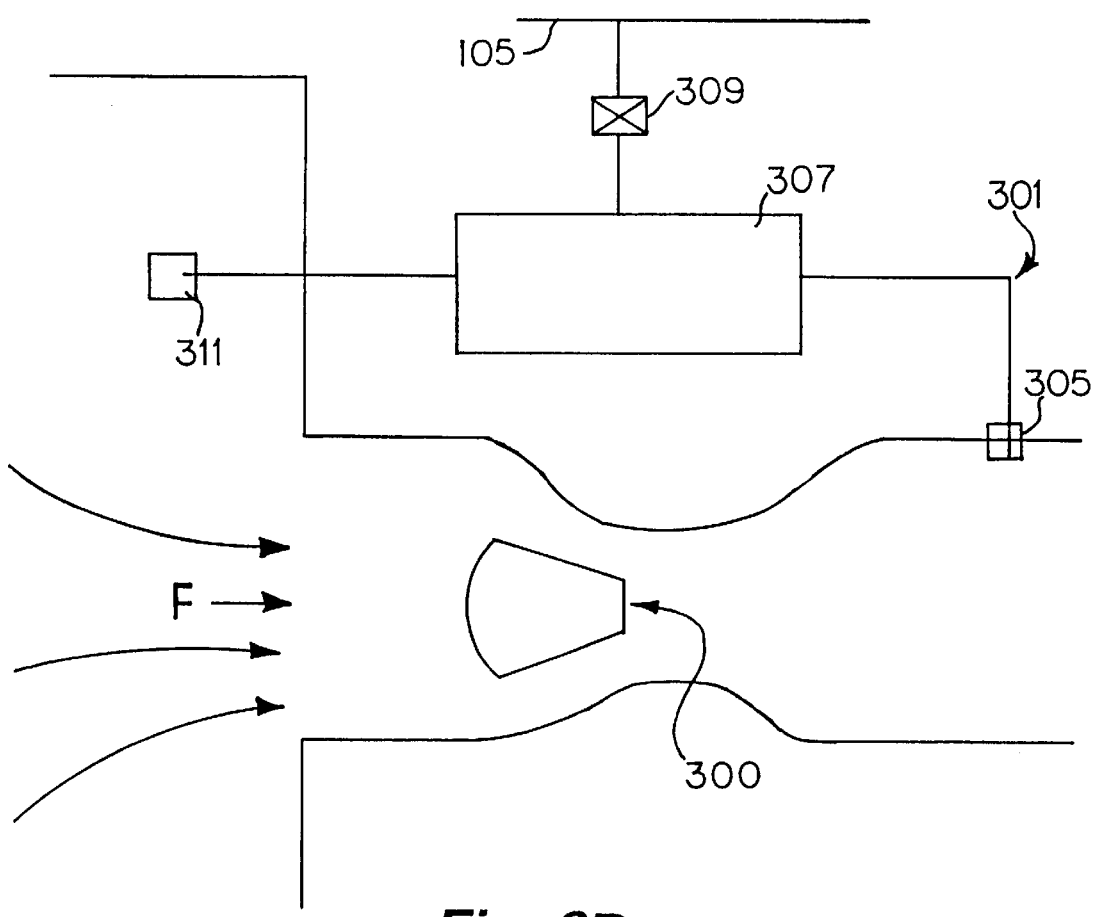

As shown in FIG. 3B, the averaging air intake valve 301 may have a sampling head 311 located within the space whose air quality is of concern, instead of pressure tap 303. This configuration will measure the average flow of airborne substances through the space exhausted through exhaust valve 300, e.g. a room.

Figure 3C:
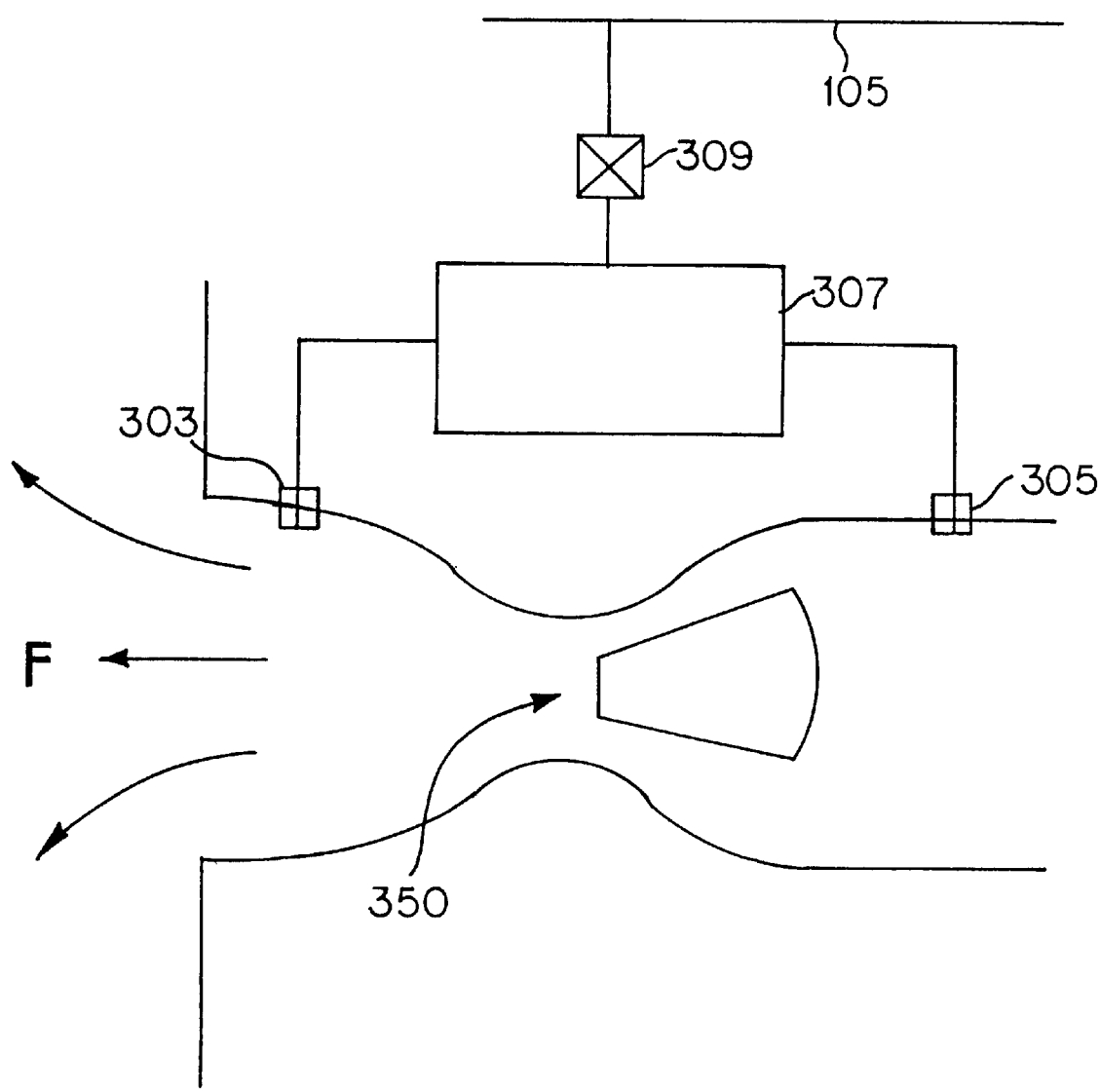

In yet another variation, there is shown in FIG. 3C an averaging air intake valve 301 connected to straddle an air supply valve 350 or another element causing a pressure drop in an air flow. This system operates similarly to that discussed above in connection with FIG. 3A, but measures and averages the air flow in a supply duct, rather than in an exhaust duct. This may be useful for discovering cross-contamination from other parts of an air management system, defects in the air supply system, and for controlling the make-up air supply in response to an emergency condition detected elsewhere.

Figure 4:
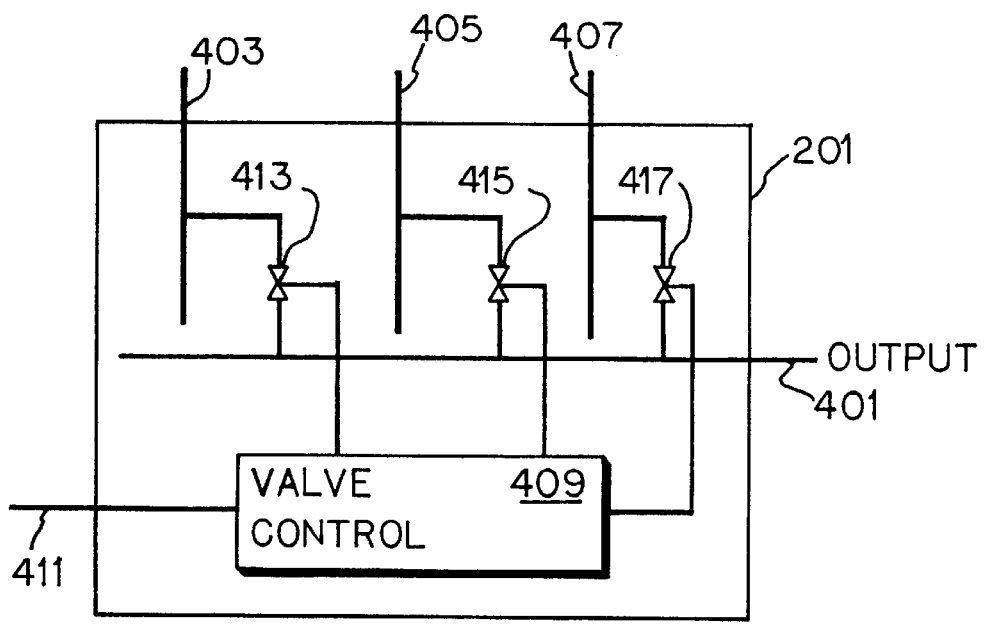
FIGS. 4A–4C are schematic drawings of air packet routers useful in some embodiments of the invention.
Figure 4:
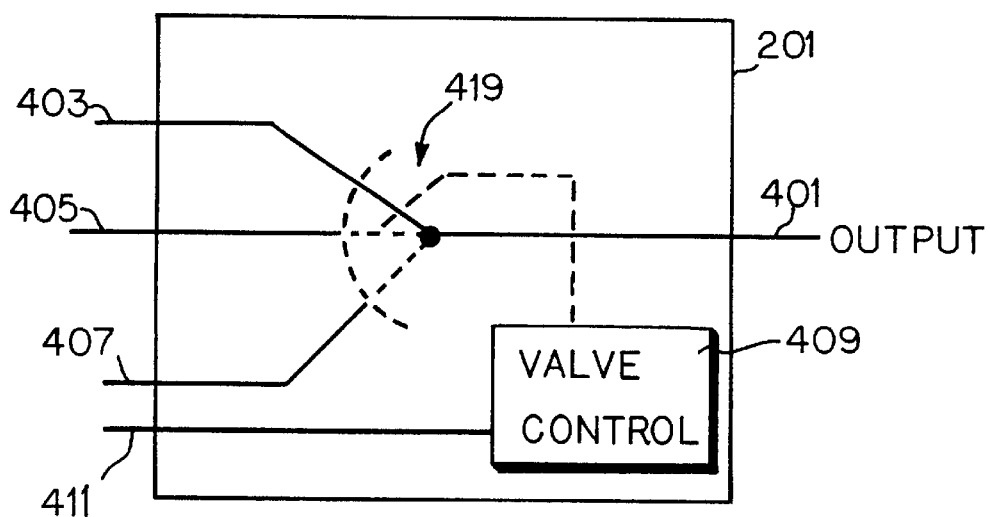
Figure 4C:
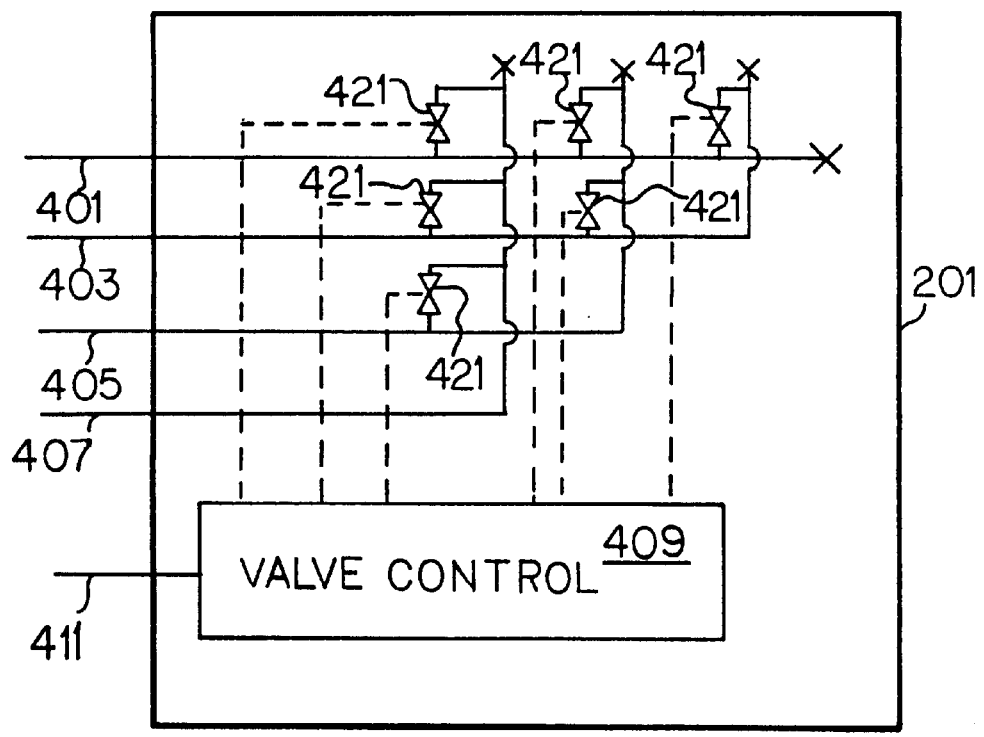

Routers suitable for application in embodiments of the invention are available in several configurations, as shown in FIGS. 4A–4C.

In FIG. 4A, a router 201 is schematically shown which has one output port 401 and three input ports 403, 405 and 407. An electronic or pneumatic valve control 409 is also included. The valve control has a control input 411, which receives a control signal indicative of the positions to which valves 413, 415 and 417 are set. Zero, one or more of valves 413, 415 and 417 may close, connecting zero, one or more of input ports 403, 405 and 407 to output port 401. Of course, it will be understood by those skilled in this art that in all descriptions of the routers 201 the designation input and output are arbitrary and may be reversed depending on the air flow and logical connections desired to be made.

In FIG. 4B, another router having one output port 41 and three input ports 403, 405 and 407 is shown. This router connects one of the three input ports 403, 405 and 407 to the output port 401 through air flow switch 419. Air flow switch 419 is controlled through valve control 409 using control signal 411, as above.

Finally, FIG. 4C illustrates a router configured to cross-connect any of four ports 401, 403, 405 and 407 with any other of the four ports. Valve control 409 operates valves 421 to make the desired connection responsive to input signal 411.

Although the network of FIG. 2 is of a simple, "fishbone" configuration, other, more complex topologies are also possible.

Figure 5:
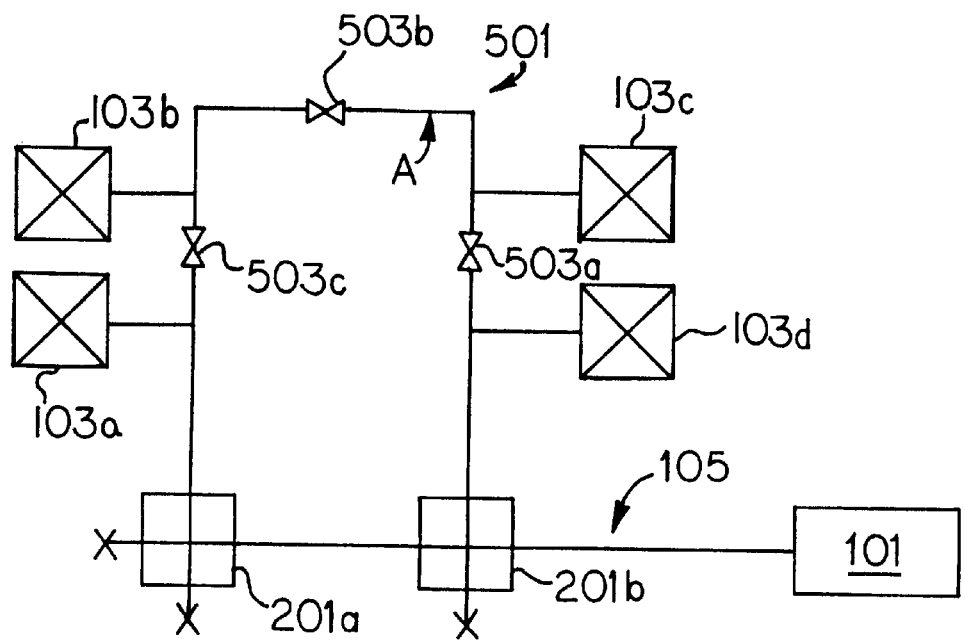
FIG. 5 is a schematic drawing of a part of an embodiment of an air sampling system illustrating a useful, alternate network topology.

The topology of FIG. 5 is one type of "self-healing" topology. As shown, a break or blockage at any point in loop 501 disrupts operation of, at most, one air intake valve 103a–103d. For example, suppose a break occurs at point A. Air intake valves 103a and 103b are sampled through router 201a, while air intake valve 103d is sampled through router 201b. Valves 503a and 503c open to isolate the break at point A, while valve 503b closes to connect air intake valve 103b to router 201a.

Figure 6:
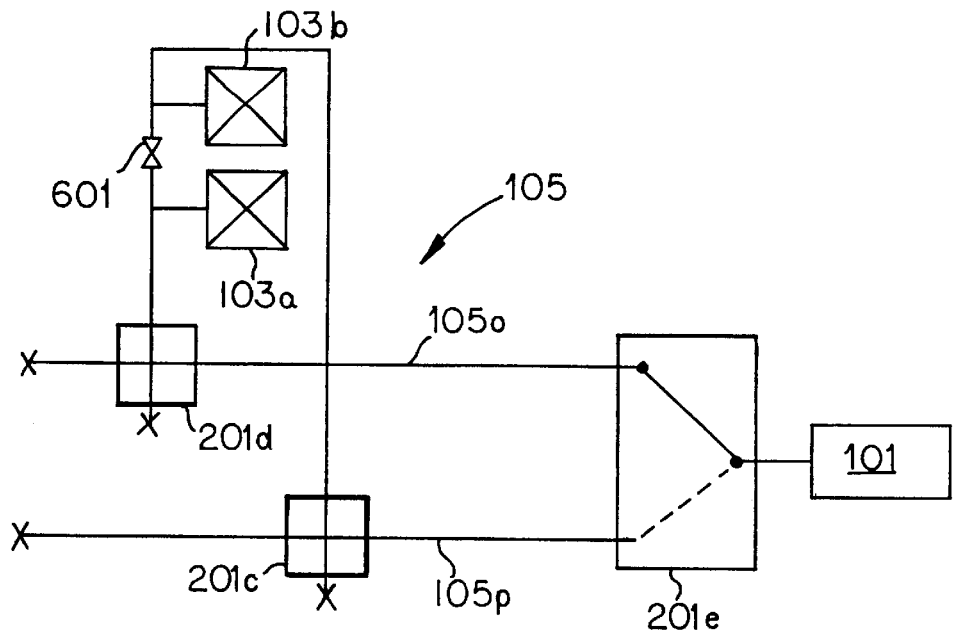
FIG. 6 is a schematic drawing of a part of an embodiment of an air sampling system illustrating another useful, alternate network topology.

An alternative, self-healing topology is shown in FIG. 6. This topology can exploit twin-tube technology in backbone segments 105o and 105p. A single break anywhere in the tubing network 105 disrupts operation of at most one air intake valve 103a, 103b. Routers 201c and 201d and valve 601 can be configured along with router 201e to isolate a break anywhere in network 105.

Now that a large number of topologies and variations of embodiments of the invention have been described, we return to the issue of pressure drop in the system. In any of the variations discussed above, booster 700 such as illustrated in FIG. 7 can be provided to maintain a safe operating pressure and flow throughout the system.

Figure 7:
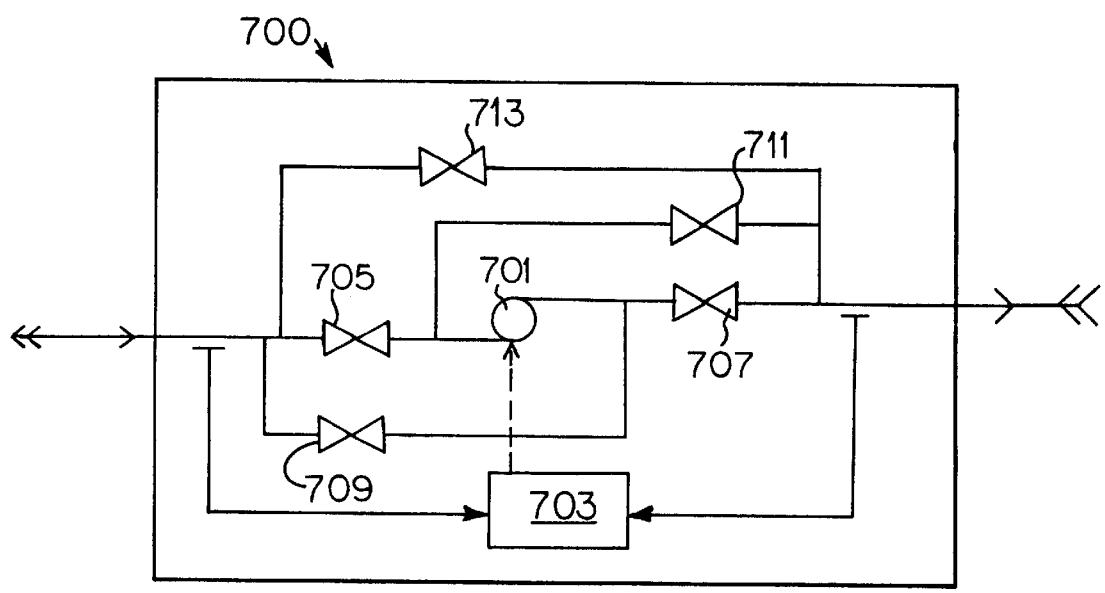
FIG. 7 is a schematic drawing of a bidirectional pressure or flow rate booster useful in some embodiments of the invention.

The booster 700 of FIG. 7 is bidirectional and includes a shunt valve 713 which can be used to bypass the boost function entirely. These boosters are advantageously included in the routers 201 of a large network, or may be placed in series with any tube of the network 105 which may benefit from a pressure or flow rate boost.

The function of booster 700 is now described in connection with FIG. 7. The booster 700 includes a pump 701 which provides the pressure or flow rate boost. The amount of boost provided is controlled by control unit 703, which controls pump motor speed, a throttle or a damper in series with the pump, for example, in response to a measurement of flow rate or pressure drop. When valves 705 and 707 are open and valves 709 and 711 are closed, the booster 700 operates in a forward direction. The booster 700 can be made to operate in a reverse direction by closing valves 705 and 707, while opening valves 709 and 711.

The various aspects of the invention described above are advantageous for several reasons not yet discussed in detail.

In each of the systems described, depending upon the relative locations of sensors, tracer gas sources and routers or valves, part of the network could carry a tracer gas at a positive pressure to an open valve while an air sample is taken under negative pressure from another open valve. For example, subnetwork backbone 105f could carry tracer gas to any valve 103 on subnetwork backbones 105f or 105i while a sample is drawn from any open valve 103 on subnetwork backbones 105g, 105h, 105j and 105k to the central sensing and control unit 101.

Each of the systems described is more flexibly configured than conventional systems because of the use of a single, central sensing and control unit 101, in connection with a network having flexible air flow routing. Flexibility is further supported by the use of a fiber optic, an electronic or a pneumatic control network run in parallel with the network of tubing 105. The control network may be of a distributed control configuration. Multiple sensing and control units 101 and 203 can be distributed throughout the system. These units can coordinate their use of the network 105 through the electronic control network run in parallel with the network of tubing 105. Of course, the electronic control network could alternatively have a different topology than that of the underlying network of tubing 105. Flexible air routing to the central sensing and control unit from air intake valves 103 permits changing air intake valve configurations merely by changing routing instructions. Also, adapting the system to detect a new parameter, such as a new contaminant is accomplished by changing only one sensor package, rather than one sensor in each room sensed.

Moreover, networked air measurement systems according to the invention are particularly suitable for inexpensive "pre-wiring" of building spaces along with other building air handling equipment. Pre-wiring and flexibility are enhanced in systems according to aspects of the invention in which a backbone serves plural branches or loops because a large number of sensing sites can be pre-wired with both tubing network 105 and with an electronic or pneumatic control network run in parallel, without necessitating a large number of individual runs back to the central sensing and control unit. Routers, air intake valves and tubing, electronic control network nodes, wiring and electronic input/output devices could all be placed in advance along with other air handling and air flow control devices. The electronic communication elements including electronic control network nodes, wiring and electronic input/output devices, ready for connection to routers, switches and control devices, could be placed in advance along with the tubing. In fact, the optic cable or wire for the control network can be bonded or otherwise fixed to the tubing before installation, so both can be installed simultaneously in the same space. Placement and connection of the network elements is thus greatly simplified. Since the other air handling and air flow control devices in a building already require some degree of access after construction is complete, access is provided for modification of the networked air measurement system.

Buildings designed to include air handling and control equipment, including devices made by Phoenix Controls Corporation, for example, are among the contemplated uses of the invention. In such a building, the inlet valves, air sample routers and tubing could be co-located with air valves, dampers, electronic control and data network routers and other devices conventionally included in the air handling and control equipment design. Where electronic control of air handling equipment from a central location is contemplated, an electronic control network may already be part of a building design. The air valves, dampers, electronic control and data network routers and other networked air measurement devices could be controlled through the contemplated electronic control data network. Alternatively, a dedicated electronic control network having a physical topology parallel to that of the underlying networked air management systems could be made part of the initial installation.

At least one aspect of the present invention avoids the problem of requiring a large number of control wires to control a corresponding number of inlet valves. In a networked approach, according to this aspect of the invention, redundancy can be reduced while maintaining a high degree of flexibility, for example in "self-healing" topologies as described above. For example, in the network of FIG. 1, the backbone section 105e is common to the delivery of samples from all four inlet valves shown in 103a–103d. Thus, the economy of not providing four separate tubing runs to the sensor suite 107 is achieved. The network of FIG. 1 can be made self-healing using the structures shown in FIGS. 5 or 6, without adding much hardware. The control network whereby the control and communication unit 111 opens and closes the inlet valves 103a–103d achieves similar economies with similar flexibility.

Figure 8:
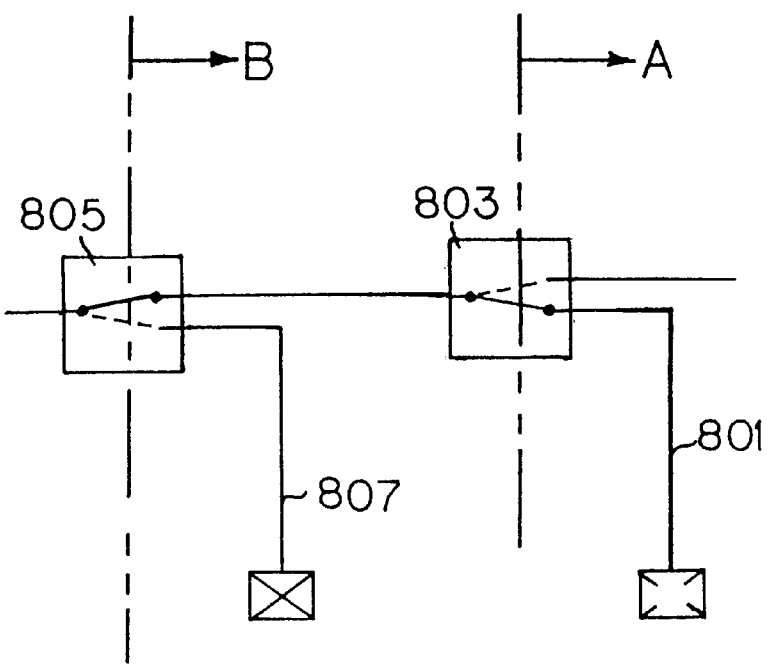
FIG. 8 is a schematic drawing of a part of an embodiment of an air sampling system illustrating a series network topology.
Figure 9:
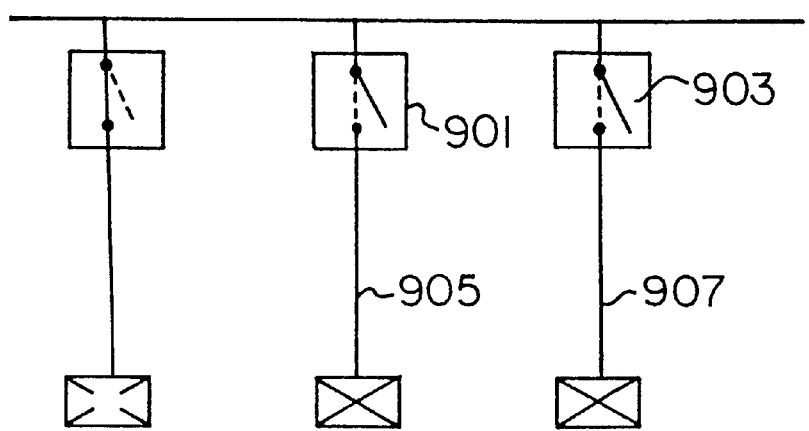
FIG. 9 is a schematic drawing of a part of an embodiment of an air sampling system illustrating a tapped line network topology.
Figure 10:
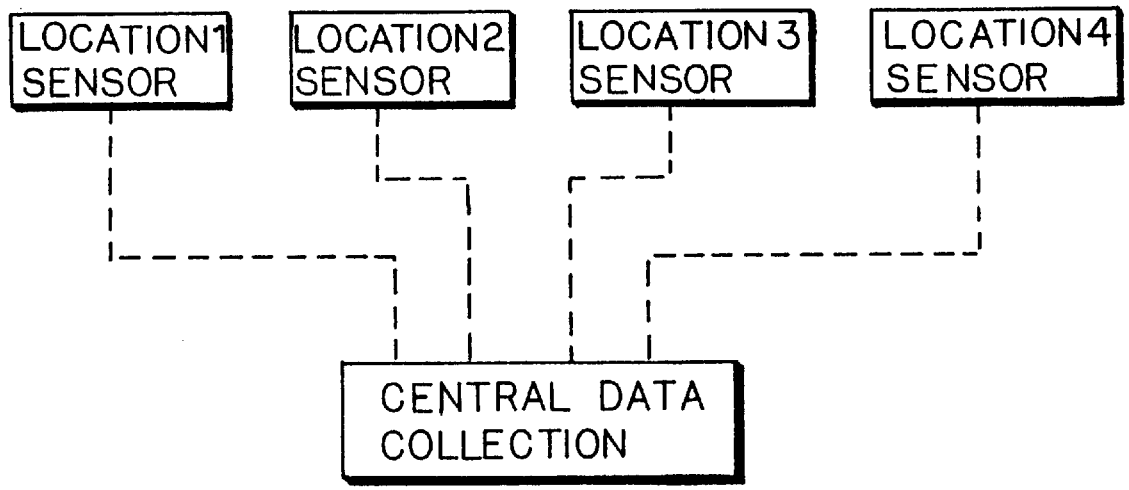
FIG. 10 is a conventional remote sensing system.
Figure 11:
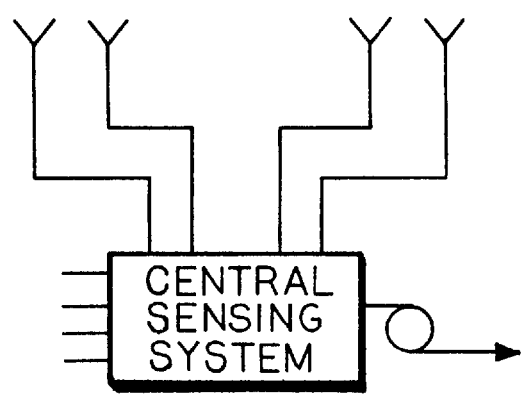
FIG. 11 is a conventional central sensing system using multiple intake tubes.

Optionally, branches of the network can be connected to a backbone section or intake tubes can be connected to branches through the valve arrangements of FIGS. 8 and 9. FIG. 8 shows a configuration which minimizes the number of valves which need to be actuated to isolate a section of the network, while FIG. 9 shows a low pressure drop configuration. Both of these configurations reduce cross-contamination between samples drawn through one branch of the network and unused branches of the network whose intake valves are shut off, making those unused branches dead-ends holding stagnant air from previous samples.

The configuration of FIG. 8 reduces cross-contamination by a series connection of valves and network sections which places a valve between each part of the network from which samples will be drawn and each part of the network which will be unaccessed at different times during operation of the network. For example, valve 803 isolates all elements of the system in region A when a sample is drawn from branch tube 801, while valve 805 isolates all elements of the system in region B (which includes region A) when a sample is drawn from branch tube 807. This configuration does, however, incur greater pressure drops from remote branches, e.g., branch 801, to the sensor unit than the configuration of FIG. 9, for example.

In the configuration of FIG. 9, the pressure drop from each intake to the backbone is minimized by minimizing the number of valves through which each sample must pass. Isolation of samples from cross-contamination may be reduced by isolating with valves 901 and 903 the branch tubes 905 and 907, respectively, when they are unused.

The invention has now been shown and described in connection with an embodiment and several variations, but is not intended to be limited thereto. For example, each of the tubes 105, etc. may be run using a twin tube material common in pneumatic applications. By using a twin tube material, greater air sample routing flexibility is attained, for example, by using the topology of FIG. 6. Furthermore, an air packet containing a tracer substance could be routed from a source to a destination in the system, while air monitoring continued in parallel in the fashion described above. By placing a valve 103 near a fume hood, and a valve 103 in the exhaust duct of the fume hood, for example, performance of critical air quality devices may be monitored by injecting tracer gases near the fume hood and measuring concentration of the tracer gases found in the exhaust flow. Inline particle filters can be used to keep the tubes from becoming clogged with particulates from the environmental air in any application not requiring detection of the particles. It may also be possible to filter large particles in an application which detects snmaller particles.

Additional variations should now be evident to those skilled in the art, and are contemplated as falling within the scope of the invention, which is limited only by the claims appended hereto and equivalents thereof.

What is claimed is:

1. A method of performing fume hood containment testing, comprising:
   selecting from a plurality of intake ports located at diverse locations and connected to a network of tubing, a first intake port at a first location in the vicinity of a fume hood work space defined by a fume hood;
   receiving a first sample into the network of tubing through the first intake port at the first location;
   controlling a valve within the network tubing responsive to the step of selecting to transport the sample from the first location to a sensor;
   detecting at the sensor a presence of a material in the vicinity of the fume hood work space; and
   introducing a tracer material into a fume hood work space;
   wherein the network of tubing includes twin tube, the method further comprising:
   supplying the tracer material through one tube of a twin tube; and
   routing the air sample through another tube of the twin tube.

2. A method of performing fume hood containment testing, using a networked building air measurement system, comprising:
   receiving an air sample through at least one air intake valve of a plurality of air intake valves, the at least one air intake valve being disposed near a fume hood work space defined by a fume hood;
   communicating the received air sample into a backbone tube in communication with an air inlet port of a sensor capable of measuring a characteristic of an air sample;
   controlling the sensor and each air intake valve in a control sequence which opens and closes each one of the plurality of air intake valves at individually defined times forming a separate air sample from each one of the plurality of air intake valves communicated through the backbone tube to the sensor; and
   transmitting communications over a communication network including a common medium connecting the controller to the air intake valves so the controller can address messages over the common medium to one of the air intake valves.

3. The method of claim 2, further comprising:
   simulating an obstruction to air flow at a defined location.

4. The method of claim 3, further comprising: locating the intake port on the obstruction to air flow.

5. The method of claim 4, simulating further comprising:
   occupying the defined location with a manikin.

6. The method claim 4, further comprising:
   removably connecting the intake port to a fixed receptacle connected to the network of tubing.

7. The method of claim 2, further comprising:
   receiving an air sample through another air intake valve located away from the fume hood work space.

8. The method of claim 7, wherein the location away from the fume hood work space is adjacent another fume hood work space.

9. The method of claim 2, wherein the at least one air intake valve is located on the fume hood.

10. A fume hood containment testing system in a building comprising:
    a sensor capable of measuring a characteristic of an air sample including a characteristic indicative of a loss of containment in a fume hood work space defined by a fume hood, the sensor having an air inlet port;
    a backbone tube in communication with the air inlet port of the sensor;
    a plurality of air intake valves remotely disposed from each other relative to distances within the building and in communication with the backbone tube such that air admitted through one of the plurality of air intake valves is communicated into the backbone tube including one air intake valve located near the fume hood work space;
    a controller connected to the sensor and to each air intake valve, the controller executing a control sequence which opens and closes each one of the plurality of air intake valves at individually defined times forming a separate air sample from each one of the plurality of air intake valves communicated through the backbone tube to the sensor; and
    a communication network including a common medium connecting the controller to the air intake valves so the controller can address messages over the common medium to one of the air intake valves.

11. The system of claim 10, wherein the one air intake valve is located on the fume hood.

12. The system of claim 10, wherein the controller is connected to the sensor and to each air intake valve through a communication network, the control sequence executed by the controller further for transmitting commands through the communication network.

13. The system of claim 10, wherein the controller executes a control sequence which in a first mode opens and closes each one of the plurality of air intake valves at individually defined times forming a separate air sample from each one of the plurality of air intake valves communicated through the backbone tube to the sensor.

14. The system of claim 13, wherein the controller executes the control sequence in a second mode which simultaneously opens and simultaneously closes a selected plurality from the plurality of air intake valves, admitting air and forming mixed air samples communicated to the sensor.

15. The system of claim 14, wherein the controller executes a control sequence in which the second mode is entered, a measurement of a mixed sample is made by the sensor, and the first mode is entered only when the measurement of the mixed sample meets predefined criteria.

16. The system of claim 10, further comprising:
a router valve;
a plurality of branch tubes connected to the backbone tube by the router valve;
the controller coupled to the router valve to control the router valve to put any of the plurality of branch tubes in communication with the backbone tube.

17. The system of claim 10, further comprising:
a router valve;
a plurality of tubes interconnected through the router valve;
the controller coupled to the router valve to control the router valve to put any of the plurality of tubes and the backbone tube in communication with any other of the plurality of tubes and the backbone tube.

18. The system of claim 10, further comprising:
a plurality of branch tubes connected between the backbone tube and corresponding groups of air intake valves, each branch tube bringing each air intake valve of a corresponding group of air intake valves into communication with the backbone tube.

19. The system of claim 10, wherein a measurement is made by the sensor and the controller monitors the measurement to determine when a stable air sample is achieved.

20. A method of performing fume hood testing, comprising:
locating a first intake port connected to a network of tubing in a room containing a fume hood;
selecting the first intake port;
receiving a first sample into the network of tubing through the first intake port;
controlling a valve within the network of tubing, responsive to selecting, to transport the sample from the room to a sensor;
detecting at the sensor a presence of a material in the room;
introducing a tracer material into the fume hood;
supplying the tracer material through one tube of the network tubing; and
routing the first sample through another tube of the network tubing;
wherein the one tube and the another tube together comprise a twin tube.

21. A method of performing fine hood testing, comprising:
locating a first intake port connected to a network of tubing in a room containing a fume hood;
selecting the first intake port;
receiving a first sample into the network of tubing through the first intake port;
controlling a valve within the network of tubing, responsive to selecting, to transport the sample from the room to a sensor,
detecting at the sensor a presence of a material in the room;
transmitting communications over a communication network including a common medium connected to the valve so messages are addressed to the valve over the common medium during the step of controlling;
introducing a tracer material into the fume hood;
supplying the tracer material through one tube of the network tubing; and
routing the first ample through another tube of the network tubing.

22. The method of claim 21, wherein the one tube and the another tube together comprise a twin tube.

* * * * *

UNITED STATES PATENT AND TRADEMARK OFFICE
CERTIFICATE OF CORRECTION

PATENT NO.   : 6,425,297 B1
DATED        : July 30, 2002
INVENTOR(S)  : Gordon P. Sharp It is certified that error appears in the above-identified patent and that said Letters Patent is hereby corrected as shown below:

Column 12,
Line 15, please replace "AGHRAE" with -- ASHRAE --.

Column 17,
Line 24, please replace "snmaller" with -- smaller --.

Column 20,
Line 13, please replace "fine" with -- fume --.
Line 21, please replace "sensor," with -- sensor; --.
Line 31, please replace "ample" with -- sample --.

Signed and Sealed this

First Day of October, 2002

*Attest:*

JAMES E. ROGAN
Director of the United States Patent and Trademark Office

*Attesting Officer*